US00PP33981P2

(12) United States Plant Patent
Smith

(10) Patent No.: US PP33,981 P2
(45) Date of Patent: Mar. 1, 2022

(54) ***CHRYSANTHEMUM* PLANT NAMED 'CIFZ0084'**

(50) Latin Name: ***Chrysanthemum* x *morifolium***
Varietal Denomination: CIFZ0084

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/233,584

(22) Filed: Apr. 19, 2021

(51) Int. Cl.
*A01H 5/02* (2018.01)
*A01H 6/14* (2018.01)

(52) U.S. Cl.
USPC ..... Plt./293

(58) Field of Classification Search
USPC ..... Plt./287, 292, 293
See application file for complete search history.

*Primary Examiner* — Susan McCormick Ewoldt
(74) *Attorney, Agent, or Firm* — Dale Skalla

(57) ABSTRACT

A new garden type *Chrysanthemum* plant named 'CIFZ0084' particularly distinguished by its small size plant with round mound plant habit, a small size decorative flower, purple flower color and a natural season response in mid September.

1 Drawing Sheet

Latin name of the genus and species of the plant claimed: *Chrysanthemum* x *morifolium.*

Varietal denomination: 'CIFZ0084'.

BACKGROUND OF THE NEW PLANT

The present invention comprises a new *Chrysanthemum*, botanically known as *Chrysanthemum* x *morifolium*, and hereinafter referred to by the variety name 'CIFZ0084'.

'CIFZ0084' is a product of a planned breeding program. The new cultivar has small size plant with round mound plant habit, a small size decorative flower, purple flower color and a natural season response in mid September.

'CIFZ0084' originated from small lots of remnant seed that had been made from 2007 through 2010 either in Salinas, Calif. or Tenjo, Columbia. Seeds were sown together as a group in November 2016 in Gilroy, Calif. with the goal of selecting red and purple seedlings and 'CIFZ0084' was selected from the resulting population on Mar. 22, 2017 in Alva, Fla.

As both parents are unknown, a comparison of male and female with 'CIFZ0084' is not possible.

The first act of asexual reproduction of 'CIFZ0084' was accomplished when vegetative stem cuttings were propagated from the initial selection in May 2017 in Alva, Fla.

BRIEF SUMMARY OF INVENTION

Horticultural examination of plants grown from cuttings of the plant initiated in May 2017 and continuing thereafter, has demonstrated that the combination of characteristics as herein disclosed for 'CIFZ0084' are firmly fixed and are retained through successive generations of asexual reproduction.

'CIFZ0084' has not been observed under all possible environmental conditions. The phenotype may vary significantly with variations in environment such as temperature, light intensity and day length.

A Plant Breeder's Right for this cultivar has not been applied for. 'CIFZ0084' has not been made publicly available prior to the effective filing date of this application, notwithstanding any disclosure that may have been made less than one year prior to the effective filing date of this application by the inventor or another who obtained 'CIFZ0084' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0084' with colors being as true as possible with an illustration of this type.

Figure 1:
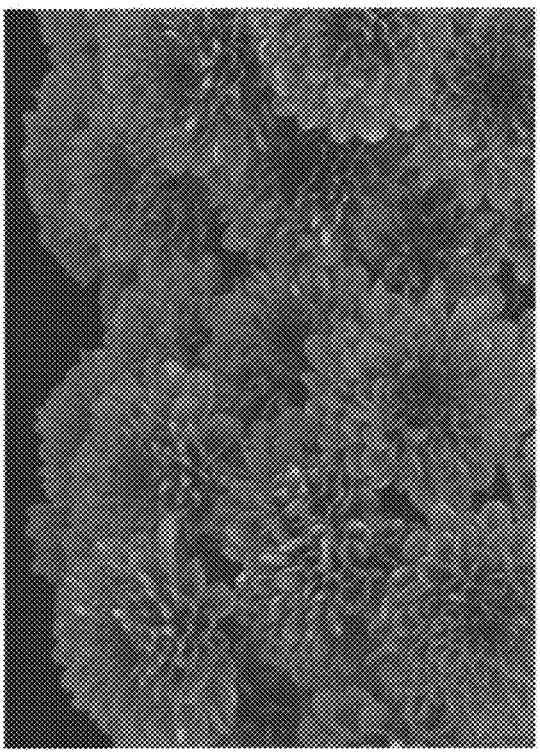
Figure 2:
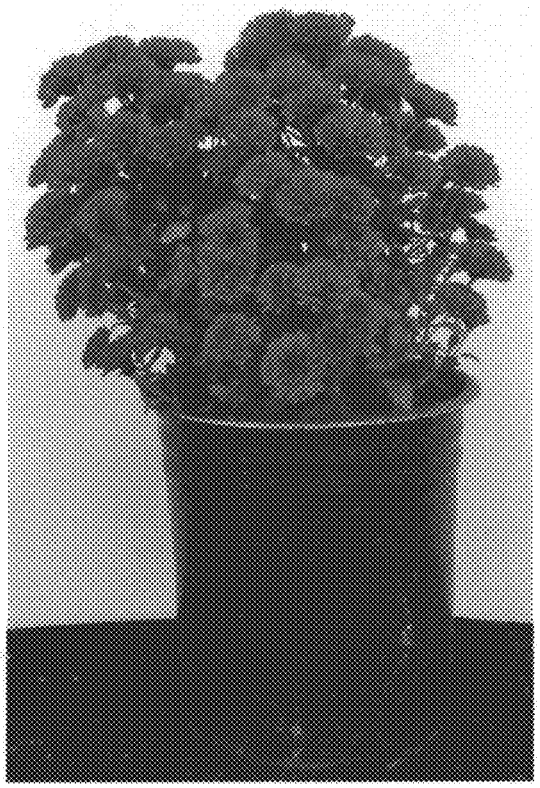

The photographic drawing shows in FIG. 1 a close view of flower of the new variety and in FIG. 2 a flowering plant from an indoor trial.

The aforementioned photographs: FIG. 1, as well as FIG. 2, were taken in March 2021 both showing a plant from the same blackcloth indoor trial in Enkhuizen, The Netherlands.

These plants were about 10 weeks of age. One rooted cutting per pot had been planted in a one gallon pot, not pinched in week 53, 2020 and black clothed from week 3. Plants started flowering mid March 2021.

DETAILED BOTANICAL DESCRIPTION

The measurements were taken in Gilroy, Calif. in November 2020 on the plants from an indoor blackcloth trial.

Color references are made to The Royal Horticultural Society Colour Chart (R.H.S.) 2015.

TABLE 1

DIFFERENCES BETWEEN THE NEW VARIETY 'CIFZ0084' AND TWO MOST SIMILAR VARIETIES:

| Trait | 'CIFZ0084' | 'CIFZ0021' (U.S. Plant Pat. No. 24,025) |
|---|---|---|
| Natural response: | Similar but more time from bud color to open flowers | Similar but less time from bud color to open flowers |
| Blackcloth response: | Similar | Similar |
| Flower size: | Similar | Similar |
| Flower color: | Purple so darker color | Dark pink/lavender so lighter color |
| Flower type: | Similar | Similar |
| Plant size: | Bit larger overall | Bit smaller overall |
| Plant habit: | More upright in blackcloth | Less upright in blackcloth |
| Flower longevity: | Slightly more | Slightly less |
| Flowering uniformity: | More uniform flowering | Less uniform flowering |

TABLE 2

| Trait | 'CIFZ0084' | 'Adiva Purple' (U.S. Plant Pat. No. 22,831) |
|---|---|---|
| Natural response: | ½ week faster | ½ week slower |
| Blackcloth response: | Similar | Similar |
| Flower size: | Similar | Similar |
| Flower color: | Purple so darker color | Dark pink/lavender so not as dark in color |
| Flower type: | Similar | Similar |
| Plant size; | Bit larger | Bit smaller |
| Plant habit: | Similar | Similar |
| Flower longevity: | 20% longer | 20% shorter |

Plant:

*Form, growth and habit.*—Herbaceous garden-type, stems Upright and outwardly spreading, freely branching, strong and moderately vigorous growth habit.

*Plant height (above soil).*—18-21 cm.

*Plant height (inflorescence included).*—19-22 cm.

*Plant width.*—24 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137A.

*Immature leaf, color lower surface.*—RHS 137D.

*Mature leaf, color, upper surface.*—RHS NN137B.

*Mature leaf, color lower surface.*—RHS NN137D.

*Length.*—3.5 cm.

*Width.*—2.0 cm.

*Shape.*—Ovate, with distinct lobes.

*Base shape.*—Attenuate.

*Apex shape.*—Mucronate.

*Margin.*—5-lobed (palmate), edge dentate.

*Number of margin indentations.*—Few.

*Depth of margin indentations.*—Medium.

*Leaf length terminal lobe relative to total leaf length.*—Short.

*Leaf depth lower lateral sinus.*—Shallow.

*Texture, upper surface.*—Bifid hairs.

*Texture, lower surface.*—Bifid hairs.

*Color of veins, upper surface.*—RHS 138B.

*Color of veins, lower surface.*—RHS 138A.

*Pattern of veining.*—Palmate.

*Petiole color.*—RHS 137B.

*Petiole length.*—1.0-1.1 cm.

*Diameter.*—0.2-0.3 cm.

*Texture.*—Bifid hairs.

*Presence of stipules.*—Yes.

*If present, size of stipules.*—Small.

Stem:

*Quantity of main branches per plant.*—6-8.

*Color of stem.*—RHS 138A.

*Length of stem.*—7.0-8.0 cm.

*Diameter.*—0.5 cm.

*Length of internodes.*—0.5-3.0 cm.

*Texture.*—Bifid hairs.

*Color of peduncle.*—RHS 138A.

*Length of peduncle.*—3.5-4.0 cm.

*Peduncle diameter.*—0.2-0.3 cm.

*Texture.*—Bifid hairs.

Inflorescence:

*Type.*—Compositae, solitary, decorative-type inflorescences borne terminally above foliage, ligulate ray florets arranged acropetally on a capitulum giving a double flower.

*Quantity of short days to flowering (response time).*—Approximately 7 weeks.

*Natural season flowering.*—Mid September.

*Quantity of inflorescences per plant.*—70-100 with many small buds developing.

*Lastingness of individual blooms on the plant.*—About seven weeks from first color.

*Fragrance.*—Slightly spicy.

Bud (when showing color):

*Color.*—RHS N79B.

*Length.*—0.8-0.9 cm.

*Width.*—0.7-0.8 cm.

*Shape.*—Oblate.

Immature inflorescence (at moment of opening):

*Diameter.*—1.9-2.2 cm.

*Color of ray florets, upper surface.*—RHS 59A; darkest at apex.

*Color of ray florets, lower surface.*—RHS N75A.

Mature inflorescence:

*Diameter.*—3.5 cm.

*Depth.*—1.0 cm.

*Total diameter of disc.*—0.5 cm to no disk present.

*Receptacle color.*—RHS 138A.

*Receptacle height.*—0.6 cm.

*Receptacle diameter.*—1.0 cm.

*Length of corolla tube.*—Short.

Ray florets:

*Average quantity of florets.*—150-160 in several whorls.

*Color of florets, upper surface.*—RHS 64A.

*Color lower surface.*—RHS 75A.

*Length.*—1.4 cm.

*Width/diameter.*—0.5-0.6 cm.

*Shape.*—Elliptical.

*Apex shape.*—Mostly obtuse and dentate.

*Base shape.*—Tube.

*Margin.*—Entire. Small incisions may be present at tip.

*Margin*.—Type of rolling — Weakly involute.
*Texture, upper surface*.—Papillate.
*Lower surface*.—Papillate.
*Ribs present*.—Yes.
*Number of keels*.—2.
*Profile at widest point*.—Moderately convex.
*Longitudinal axis shape*.—Reflexing.

Disc florets:
*Number of disc florets*.—0.

Inflorescence (at moment of senescence):
*Color of ray florets, upper surface*.—RHS 79A.
*Color of ray florets, lower surface*.—RHS 79D.

Phyllaries:
*Quantity*.—20-22.
*Color, upper surface*.—RHS 143C.
*Color, lower surface*.—RHS 143A.
*Length*.—0.6 cm.
*Width*.—0.1-0.2 cm.
*Shape*.—Lanceolate.
*Apex shape*.—Acute.
*Base*.—Fused.
*Margins*.—Entire.
*Texture, upper surface*.—Glabrous.
*Texture, lower surface*.—Canescent.

Reproductive organs:
*Pistil*.—One.
*Length*.—0.8 cm.
*Style color*.—RHS 150C.
*Style length*.—0.3 cm.
*Stigma color*.—RHS 7D.
*Stigma shape*.—Bi-parted.
*Ovary color*.—RHS 145C.
*Ovary length*.—0.2 cm.
*Ovary width*.—0.1 cm.

Androecium: As no disc florets are present, no androecium developed.
*Disease/pest resistance*.—Has not been determined to date.
*Hardiness*.—Has not been determined to date.

What is claimed is:

1. A new and distinct variety of *Chrysanthemum* plant named 'CIFZ0084' substantially as illustrated and described herein.

* * * * *